United States Patent [19]

Kothe

[11] Patent Number: 4,943,281
[45] Date of Patent: Jul. 24, 1990

[54] SYRINGE

[76] Inventor: Lutz Kothe, Bodmaner Str. 15, D-7760 Radolfzell 14, Fed. Rep. of Germany

[21] Appl. No.: 298,403

[22] Filed: Jan. 18, 1989

[30] Foreign Application Priority Data

Jan. 23, 1988 [DE] Fed. Rep. of Germany ... 8800767[U]
Apr. 7, 1988 [DE] Fed. Rep. of Germany ... 8804592[U]

[51] Int. Cl.$^5$ .............................................. A61M 5/32
[52] U.S. Cl. .................................. 604/192; 604/198; 604/263
[58] Field of Search ............... 604/192, 187, 263, 198, 604/164, 171

[56] References Cited

U.S. PATENT DOCUMENTS

| 4,139,009 | 2/1979 | Alvarez | 604/198 |
| 4,713,057 | 12/1987 | Huttner et al. | 604/164 |
| 4,735,618 | 4/1988 | Hagen | 604/198 |
| 4,790,828 | 12/1988 | Dombrowski et al. | 604/198 |

Primary Examiner—John D. Yasko
Attorney, Agent, or Firm—Bachman & LaPointe

[57] ABSTRACT

A syringe with a cannula and a cylindrical tube and a cannula guard, wherein the cannula guard has a protective bow which is displaceable inwardly towards the cylindrical tube to retract the cannula guard, and a recess of said bow embracing the cannula.

22 Claims, 4 Drawing Sheets

SYRINGE

The present invention relates to a syringe with a cannula and a cylindrical tube as well as a cannula guard.

Syringes are commercially available in a variety of forms and designs. As a rule, nowadays disposal syringes are used, with which the cannula is taken from a sterile pack and fitted onto a nipple of a cylindrical tube shortly before use. After use, either the entire syringe or at least the cannula is discarded.

Sleeve-shaped plastic caps are also provided for keeping the cannulas sterile. In these, as also in the other cases, the cannula guard is, however, removed quite some time before use of the syringe, so that the syringe lies unprotected on a tray or the like.

In the past, this has in many cases led to injuries, if for example the physician administering treatment reaches for a syringe during an operation without looking. Furthermore, syringes are also frequently dropped from the tray or the place where they are being kept, making them unusable or even causing personal injuries.

Particularly significant today is also the fact that after use, the syringe is placed back on a tray or thrown away unprotected. Here again, there are recurring cases of injuries to persons who subsequently come into contact with this once used syringe. This constitutes a considerable risk of infection.

The inventor has set himself the object of developing a syringe of the abovementioned type with which the cannula is protected before and also again immediately after use, so that injuries are ruled out.

It leads to the achievement of this object that the cannula guard has a protective bow, which is displaceable in direction x and has a recess or the like, which embraces the cannula or cannula tip.

The direction x is defined as the direction along the longitudinal axis of the tip against the pressure direction of the plunger, with which the medium is discharged from the syringe. This means that the protective bow is guided along the cannula and consequently embraces the latter at least partially in every position of use.

It is essential that at least the tip of the cannula is protected, since this imparts the injuries.

Preferably the protective bow is to be in connection with a ring which embraces the cylindrical tube and is likewise displaceable in the abovementioned direction. As a result, a certain guidance of the protective bow is ensured.

The protective bow is in connection with further bows, the other end of which is fixed in position with respect to the cylindrical tube. These bows are in each case curved outward in the form of eyelets and consist of a flexible material. For use of the syringe, these bows are pressed inward, i.e. toward the longitudinal axis of the syringe. By the pressing-in, the bows are bent straight to a certain extent, so that the distance between their two ends, of which the one is connected to the protective bow and the other is fixed in position with respect to the cylindrical tube, is enlarged. As a result, the displacing of the protective bow in direction x, i.e. opposite to the plunger movement, takes place, so that the protective bow runs along the cannula and the latter can emerge from the protective bow.

Wherever a ring connects the protective bow it is of course provided that the bows are fastened on this ring and not directly on the protected bow.

The positional fixing of the bows with respect to the cylindrical tube is preferably performed via a disk, which is arranged between the cannula and an attachment piece for the cannula and the cylindrical tube.

In this region there is as a rule a nipple, onto which the attachment with cannula is fitted. In the present exemplary embodiment, the disk surrounds this nipple, the nipple passing through a central bore in the disk. Since, as a rule, the cylindrical tube is closed off by a cover, out of which the nipple is also formed, the disk thus lies between attachment and cover.

In order to prevent an unwanted movement of the protective bow, the disk is designed as a blocking device with respect to the protective bow. For this purpose, the disk is seated in undercuts of the protective bow, so that the latter rests for example with frame strips on the disk.

For releasing this blocking mechanism, the disk has segment cutouts which, in initial position of the syringe, do not clear a movement of the protective bow or of the frame strips. If, on the other hand, a pressure is exerted on the bows, a rotation of the disk take$ place to a certain extent until the segment cutouts come to lie under the frame strips and the latter can engage into the segment cutouts. Consequently, the frame strips can slide along the segment cutouts in direction x and the protective bow clears the cannula or the cannula tip.

If the pressure on the bows is discontinued, due to the spring-back effect of the bows, the protective bow as well is displaced into it$ initial position, so that the disk can al$o assume its stop location again. Consequently, the cannula tip is guarded again immediately after use and cannot cause any injury.

For better guidance of the protective bow, it is provided that the latter is firstly connected to a first guide ring, which then in turn has a connection via side strips to another ring, on which the bows are fixed.

In order to be able to operate the cannula guard also with one hand while at the same time dispensing the medium, according to the invention gripping eyelets are integrally attached to the bows, it being possible for a middle finger and an index finger to be inserted in each ca$e into the gripping eyelet$, while the thumb exerts the pressure on the plunger.

Any known syringe may be used as syringe. The use of disposable syringes is preferred in particular.

In practice, difficulties have been found to a slight extent due to the protective bow upon insertion of the cannula into a corresponding ampoule. In an improved embodiment of the invention, therefore the cannula guard is to either have an integrated adaptor or is to be assigned an adaptor which has in each case a corresponding annular collar or the like for receiving an ampoule. The ampoule is then inserted into the annular collar shaped accordingly to match it and the protective bow of the cannula guard is released so that the syringe can enter through the recess into the closure of the ampoule. As a result, the medicament can be sucked out of the ampoule.

In one embodiment of the invention, the annular collar is integrally attached directly to the protective bow and surrounds the recess.

In the other embodiment, however, the adaptor is to be separate from the protective bow, it consisting of a cap part and the annular collar. The cap part is in turn adapted in its inner contour to the apex of the protective bow. In particular, it is provided here that corresponding holding claws or the like are provided in the cap part for fixing on the protective bow. This adaptor facilitates use of the disposable syringe with cannula guard.

Further advantages, features and details of the invention emerge from the following description of preferred exemplary embodiments and with reference to the drawing, in which.

Figure 1:
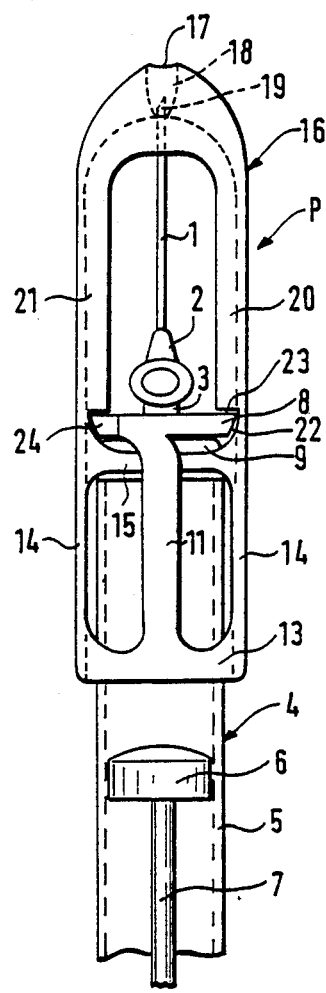
FIG. 1 shows a side view of a cannula guard according to the invention, in position for use.

A cannula guard P according to the invention serves to guard a cannula 1, which is fitted via a corresponding attachment 2 on a nipple 3 of a disposable syringe 4 or the cylindrical tube 5 of the latter. In this cylindrical tube 5 there slides a plunger 6, to which pressure can be applied via a rod 7, the medium present in the cylindrical tube 5 being discharged through the cannula 1.

Figure 2:
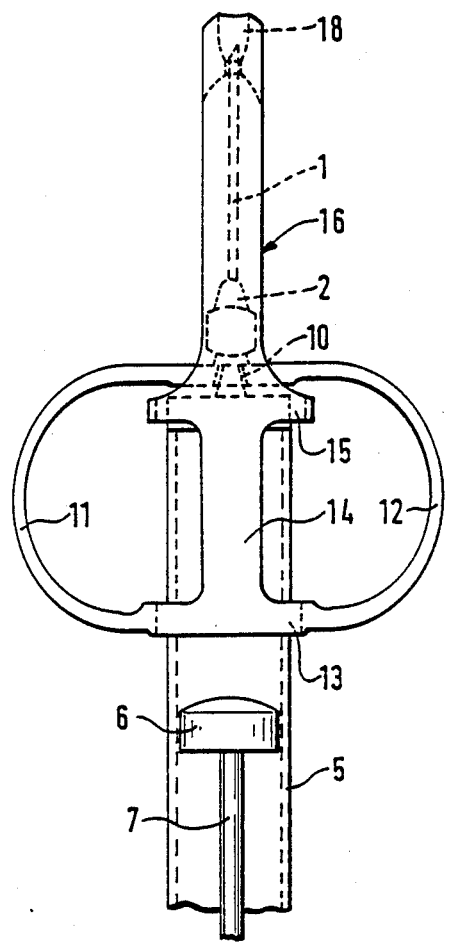
FIG. 2 shows an elevation of the cannula guard according to FIG. 1.

The cannula guard P according to the invention has a disk 8, which bears against a cover 9, which closes the cylindrical tube 5 and from which the nipple 3 rises. In this arrangement, the nipple 3 passes through a central bore 10 in the disk 8, as is indicated in FIG. 2.

From the disk 8 there protrude laterally on opposite sides two bows 11 and 12, which consists of a flexible material. These bows 11 and 12 lead to a ring 13, which surrounds the cylindrical tube 5. This ring 13 is in turn in connection via side strips 14 with a further ring 15, embracing the cylindrical tube 5. This ring 15 is arranged closely underneath the disk 8.

From this ring 15 rises the actual protective bow 16 for the cannula 1. In this case, the protective bow 16 is formed in the manner of an arch and has on its apex 17 a recess 18, into which a tip 19 of the cannula 1 partially engages.

The protective bow 16 has two frame strips 20 and 21, leading from the apex 17. These frame strips 20 and 21 have in each case a constriction 22 with respect to the ring 15, which constrictions form undercuts 23 for receiving the disk 8. Consequently, in the initial position shown in FIG. 1, the frame strips 20 and 21 rest on the disk 8, so that this disk 8 forms something of a catch.

Figure 3:
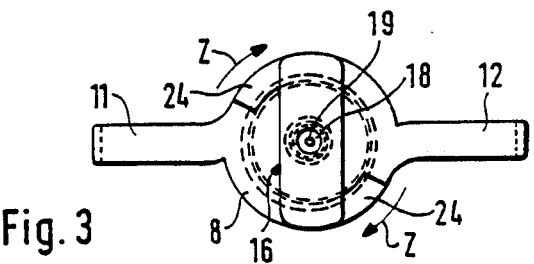
FIG. 3 shows a front view of the cannula guard according to FIG. 1.
Figure 4:
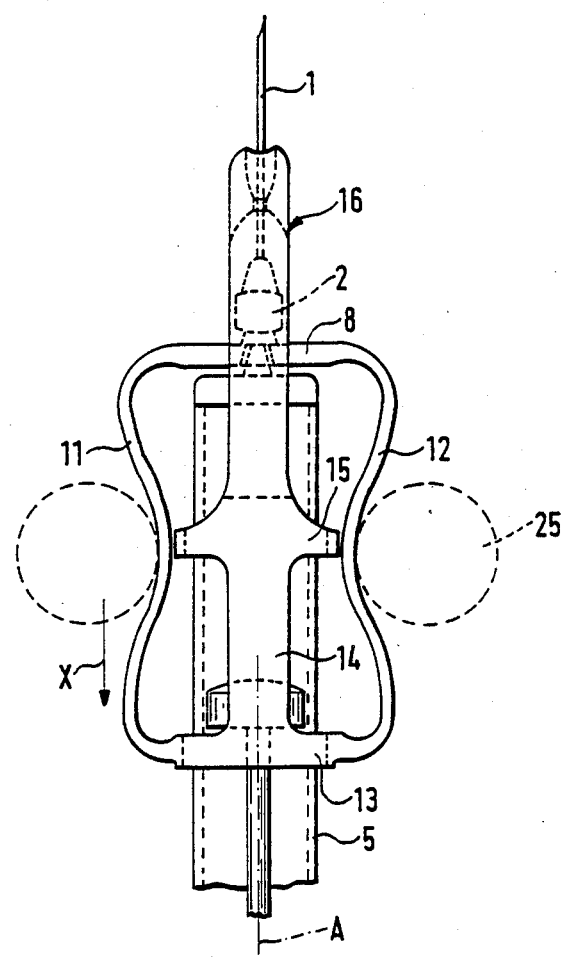
FIG. 4 shows an elevation of the cannula guard corresponding to FIG. 2 in a further position for use.

For extending the cannula 1 out of the protective bow 16 through the recess 18, as is shown more clearly in FIG. 4, the two bows 11 and 12 are pressed in toward a longitudinal axis A of the disposable syringe 4. In this action, the cannula guard P supports itself via the disk 8 against the attachment 2. Simultaneously with the pressing-in of the bows 11 and 12, a rotation of the disk 8 in direction Z also takes place, as is indicated in FIG. 3. As a result, two segment cutouts 24 of the disk 8 go into a position in which they come to lie under the frame strips 20 and 21 and clear the latter. The protective bow 16 is thus disengaged.

The disengagement of the protective bow 16 enables the ring 13 to comply to the pressure of the bows 11 and 12 and it moves in direction x along the cylindrical tube 5. In so doing, it also takes the ring 15 with it via the side strips 14. The ring is followed by the integrally attached protective bow 16.

If the pressure on the bows 11 and 12 is discontinued, they move back into their initial position shown in FIG. 2 and in so doing take the ring 13 with them. The frame strips 20 and 21 also reach their initial position, so that the disk 8 can move against the direction of rotation z and moves underneath the frame strips 20 and 21. This restores the blocking and the cannula 1 is once again completely guarded.

For use as a one-hand syringe, corresponding gripping eyelets 25 for fingers are also provided on the bows 11 and 12.

Figure 5:
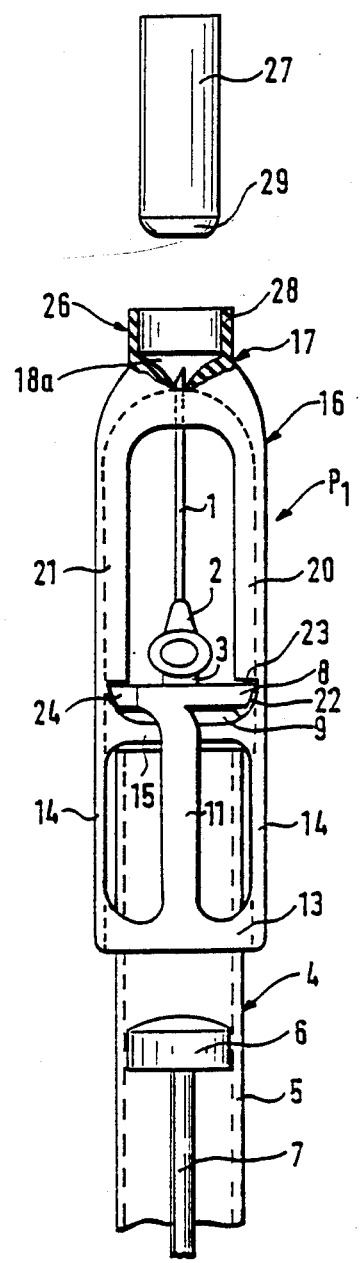
FIG. 5 shows a side view of a further exemplary embodiment of the cannula guard according to the invention, in position for use.
Figure 6:
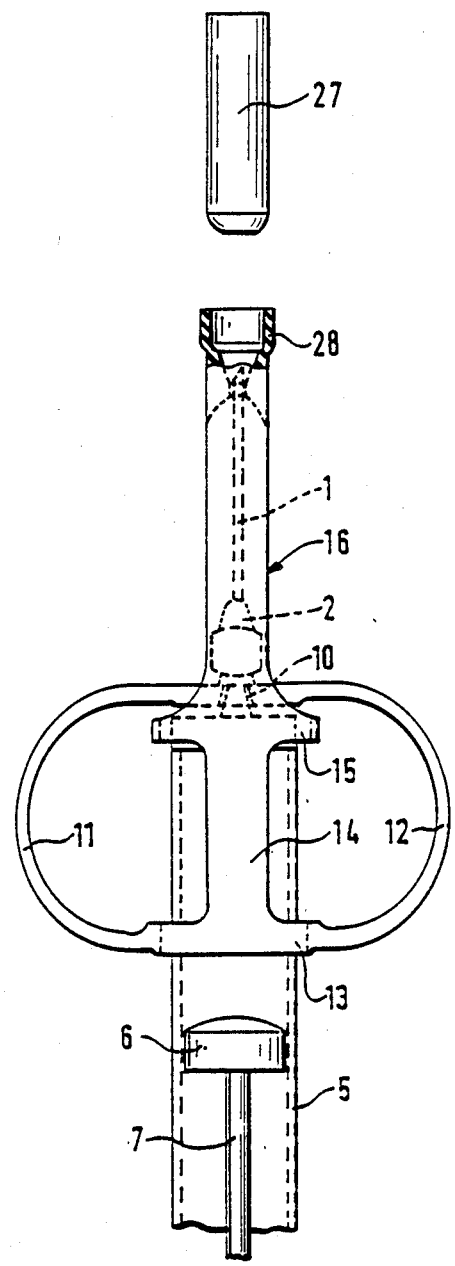
FIG. 6 shows an elevation of the exemplary embodiment of the cannula guard according to FIG. 5.

According to FIGS. 5 and 6, the protective bow 16 has in the region of its apex 17 an integrated adaptor 26. In the position for use, this integrated adaptor 26 serves to receive an ampoule 27. For the sake of simplicity, an annular collar 28 is integrally attached to the protective bow 16 for this purpose, the recess 18a bulging outward. The ampoule 27 is inserted into this annular collar 28 and then the protective bow 16 is released, so that the cannula 1 can enter into the ampoule 27, possibly through a corresponding closure 29. In this way, the content of the ampoule 27 can be sucked through the cannula 1 into the disposable syringe 4.

In FIGS. 5 and 6, the annular collar 28 is of elliptical design, so that it is adapted to an ampoule 27 of the same shape. This adaptation also applies however to any other conceivable shape of the ampoule. The annular collar 28 is preferably of flexible material, so that no adaptation difficulties exist if there are inaccuracies of fit.

Figure 7:
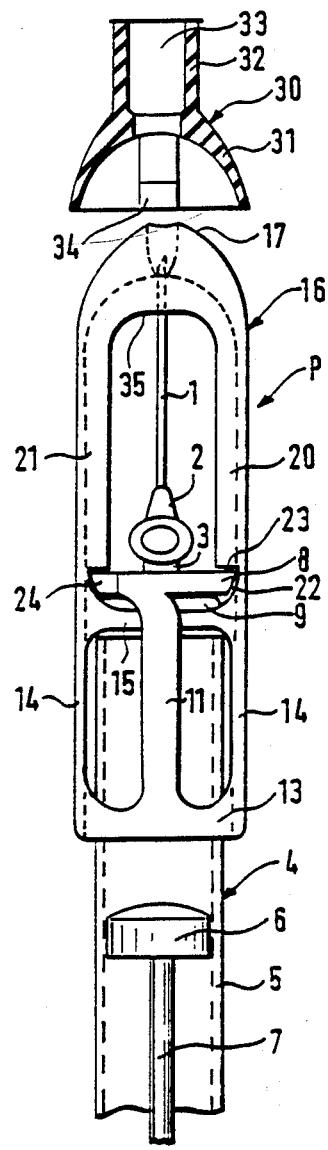
FIG. 7 shows the side view of the cannula guard according to the invention, in position for use, according to FIG. 1, with assigned adaptor.
Figure 8:
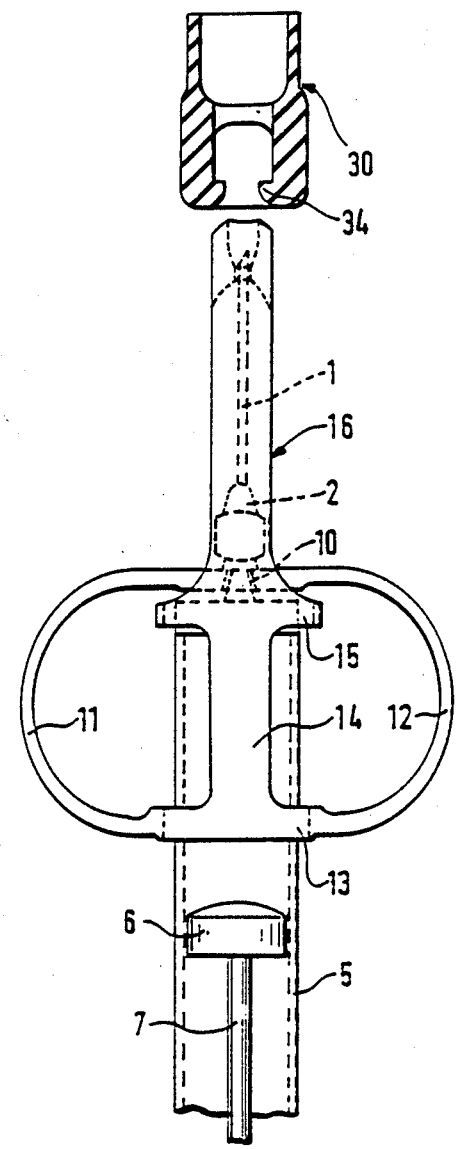
FIG. 8 shows the elevation of the cannula guard according to FIG. 2, with the adaptor according to FIG. 7.

In this context, FIGS. 7 and 8 also show another embodiment, the cannula guard P according to the invention corresponding to that according to FIGS. 1 and 2. However, this cannula guard P is assigned an adaptor 30, which is fitted when required onto the apex 17 of the protective bow 16. This adaptor 30 consists essentially of a cap part 31 and an annular collar 32, which in turn forms a receiving space 33 for an ampoule (not shown in more detail).

For better fixing of the adaptor 30, the latter has on both sides in the region of its cap part 31 holding claws 34, which, in the position for use, engage underneath a clip 35 of the protective bow 16. After filling of the disposable syringe 4, the adaptor 30 is again removed from the protective bow 16, so that the cannula 1 is accessible without difficulties.

I claim:

1. A syringe which comprises: a cannula having a cannula tip; a cylindrical tube connected to said cannula at a location spaced from said cannula tip; a cannula guard for said cannula; a protective bow of said cannula guard being displaceable inwardly towards the cylindrical tube to retract the cannula guard; and a recess of said bow embracing the cannula.

2. A syringe according to claim 1 wherein said recess embraces the cannula tip.

3. A syringe according to claim 1 including a ring in connection with the protective bow which embraces the cylindrical tube and is displaceable towards the cylindrical tube.

4. A syringe according to claim 1 including bows in connection with the protective bow having one end thereof fixed in position with respect to the cylindrical tube.

5. A syringe according to claim 4 wherein said bows are in connection with the protective bow via a ring.

6. A syringe according to claim 4 wherein the cylindrical tube has a longitudinal axis and wherein the bows consist of flexible material and can be pressed in toward said longitudinal axis.

7. A syringe according to claim 6 including a disk interconnecting said bows.

8. A syringe according to claim 7 wherein the disk is between the cannula and the cylindrical tube.

9. A syringe according to claim 8 wherein the cannula is fitted to the cylindrical tube via an attachment on a nipple, wherein the nipple is situated between the attachment and the cylindrical tube and passes through a central bore in the disk and the disk supports itself against the attachment and the cylindrical tube.

10. A syringe according to claim 9 wherein the cylindrical tube includes a cover and the disk supports itself against said cover.

11. A syringe according to claim 7 wherein the disk is designed as a blocking device with respect to the protective bow.

12. A syringe according to claim 11 wherein the protective bow forms undercuts toward the disk.

13. A syringe according to claim 12 including frame strips of said protective bow which in an initial position rest on said disk.

14. A syringe according to claim 13 wherein said disk has segment cutouts.

15. A syringe according to claim 14 wherein the disk has a central axis and is rotatable about its central axis.

16. A syringe according to claim 15 wherein the segment cutouts are arranged such that after one rotation they receive the frame strips, which then slide in the segment cutouts in a direction towards the cylindrical tube.

17. A syringe according to claim 3 including a further guide ring between the protective bow and the ring connected to the ring via side strips.

18. A syringe according to claim 4 including gripping eyelets integrally attached to the bows.

19. A syringe according to claim 1 wherein the cannula guard includes an adaptor which has an annular collar for receiving an ampoule.

20. A syringe according to claim 19 wherein the annular collar is integrally attached to the protective bow and surrounds the recess.

21. A syringe according to claim 19 wherein the protective bow has an apex and wherein the adaptor includes a cap part which is adapted to the apex of the protective bow and to which the annular collar is integrally attached.

22. A syringe according to claim 21 wherein the cap part has holding means for fixing the adaptor on the protective bow.

* * * * *